United States Patent
Rubinsky et al.

(10) Patent No.: US 8,518,427 B2
(45) Date of Patent: Aug. 27, 2013

(54) FABRIC WITH ANTIMICROBIAL PROPERTIES

(75) Inventors: Bert H. Rubinsky, Jackson, MS (US); Herman A. Taylor, Jr., Ridgeland, MS (US)

(73) Assignee: R & T Fabric, LLC, Ridgeland, MI (US)

( * ) Notice: Subject to any disclaimer, the term of this patent is extended or adjusted under 35 U.S.C. 154(b) by 0 days.

(21) Appl. No.: 13/207,392

(22) Filed: Aug. 10, 2011

(65) Prior Publication Data

US 2012/0087951 A1    Apr. 12, 2012

Related U.S. Application Data

(60) Provisional application No. 61/372,168, filed on Aug. 10, 2010.

(51) Int. Cl.
- *A01N 25/08* (2006.01)
- *A01N 65/44* (2009.01)
- *A01N 55/02* (2006.01)
- *A01P 1/00* (2006.01)
- *D03D 15/00* (2006.01)
- *B32B 9/02* (2006.01)

(52) U.S. Cl.
USPC .......... 424/404; 424/750; 424/618; 442/123; 442/152; 442/231; 442/63

(58) Field of Classification Search
None
See application file for complete search history.

(56) References Cited

U.S. PATENT DOCUMENTS 5,985,301 A * 11/1999 Nakamura et al. ............ 424/404
2007/0087162 A1 * 4/2007 Mandawewala ................ 428/97

OTHER PUBLICATIONS

Erdumlu N., Ozipek B.; Investigation of Regenerated Bamboo Fibre and Yarn Characteristics. FIBRES & TEXTILES in Eastern Europe 2008, vol. 16, No. 4 (69) pp. 43-47.*

Gaoxing Luo, Jin Tang, Weifeng He, Jun Wu, Bing Ma, Xihua Wang, Xiwei Chen, Xiaorong Zhang, Xianchang Li, Mark Fitzgerald. Antibacterial effect of dressings containing multivalent silver ion carried by zirconium phosphate on experimental rat burn wounds. Wound Rep Reg (2008), 16, 800-804.*

English language translation of: Xu Jiong and Wang Xuejie, Chinese Patent Application 01117634, Application Date Apr. 30, 2001. Note that this is a machine translation from SIPO and Google translate.*

Nazan Erdumlu and Bulent Ozipek. Investigation of Regenerated Bamboo Fibre and Yarn Characteristics. FIBRES & TEXTILES in Eastern Europe 2008, vol. 16, No. 4 (69) pp. 43-47.*

* cited by examiner

*Primary Examiner* — Frederick Krass
*Assistant Examiner* — Michael P Cohen
(74) *Attorney, Agent, or Firm* — McNeely, Hare & War LLP; Kevin J. McNeely

(57) ABSTRACT

A method of producing a fabric with antimicrobial properties that includes liquefying bamboo to produce a slurry, adding an antimicrobial element to the slurry, adding a non-bamboo fiber to the slurry to create a mixture and extruding the mixture to produce a fiber. The antimicrobial fabric may include a composition of 69% bamboo, 30% cotton and 1% silver.

11 Claims, 6 Drawing Sheets

Figure 2

Pseudomonas aeruginosa ATCC# 9027: Initial Count: 8.1 x 10$^6$

| Lab# | Sample Identification | | Pseudomonas aeruginosa ATCC# 9027 cfu/ml | | Fold Growth |
|---|---|---|---|---|---|
| | | | Contact Time 0 Hours | Contact Time 24 Hours | |
| 89639 | Control (Green) | AVG* | 7.9 x 10$^5$ | 1.7 x 10$^7$ | 215X |
| QC | In lab untreated fabric | AVG* | 4.3 x 10$^5$ | 3.1 x 10$^7$ | 720X |
| 89640 | B++ (White) | AVG* | 1.9 x 10$^4$ | 8.5 x 10$^5$ | 45X |

Figure 3

Staphyloccocus aureus MRSA ATCC# 43300: Initial Cont: 7.1 x 10$^6$

| Lab# | Sample Identification | | Staphyloccocus aureus MRSA ATCC# 43300 cfu/ml | | Fold Growth |
|---|---|---|---|---|---|
| | | | Contact Time 0 Hours | Contact Time 24 Hours | |
| 89639 | Control (Green) | AVG* | 1.9 x 10$^6$ | 2.7 x 10$^9$ | 1400X |
| QC | In lab untreated fabric | AVG* | 2.0 x 10$^6$ | 3.7 x 10$^9$ | 1850X |
| 89640 | B++ (White) | AVG* | 1.6 x 10$^6$ | 4.1 x 10$^6$ | 2.5X |

| Lab# | Sample Identification | | Staphyloccocus aureus MRSA AATCC# 43300 cfu/ml | | Fold Growth |
|---|---|---|---|---|---|
| | | | Contact Time 0 Hours | Contact Time 24 Hours | |
| 89639 | Control (Green) | AVG* | 1.9 x 10$^6$ | 2.7 x 10$^9$ | 1400X |
| QC | In lab untreated fabric | AVG* | 2.0 x 10$^6$ | 3.7 x 10$^9$ | 1850X |
| 89641 | B++ Bandage (Thick) | AVG* | 2.1 x 10$^6$ | 1.2 x 10$^8$ | 57X |

Figure 4
Klesiella pneumoniae ATCC# 4352: Initial Count: 2.8 × 10$^6$

| Lab# | Sample Identification | | Klesbiella pneumoniae ATCC# 4352 cfu/ml | | Fold Growth |
|---|---|---|---|---|---|
| | | | Contact Time 0 Hours | Contact Time 24 Hours | |
| 89639 | Control (Green) | AVG* | 9.2 × 10$^4$ | 1.0 × 10$^9$ | 10,900X |
| QC | In lab untreated fabric | AVG* | 6.3 × 10$^6$ | 2.8 × 10$^8$ | 44X |
| 89640 | B++ (White) | AVG* | 8.0 × 10$^4$ | 1.8 × 10$^4$ | −4X |

| Lab# | Sample Identification | | Klesbiella pneumoniae ATCC# 4352 cfu/ml | | Fold Growth |
|---|---|---|---|---|---|
| | | | Contact Time 0 Hours | Contact Time 24 Hours | |
| 89639 | Control (Green) | AVG* | 9.2 × 10$^4$ | 1.0 × 10$^9$ | 10,900X |
| QC | In lab untreated fabric | AVG* | 6.3 × 10$^6$ | 2.8 × 10$^8$ | 44X |
| 89641 | B++ Bandage (Thick) | AVG* | 3.3 × 10$^6$ | 1.1 × 10$^8$ | 33X |

Figure 5
Clostridium difficile ATCC# 9689: Initial Count: 2.5 × 10$^6$

| Lab# | Sample Identification | | Clostridium difficile ATCC# 9689 cfu/ml | | Fold Growth |
|---|---|---|---|---|---|
| | | | Contact Time 0 Hours | Contact Time 24 Hours | |
| 89639 | Control (Green) | AVG* | 2.7 × 10$^5$ | 2.3 × 10$^6$ | 8.5X |
| QC | In lab untreated fabric | AVG* | 2.6 × 10$^6$ | 4.8 × 10$^7$ | 18X |
| 89640 | B++ (White) | AVG* | 9.1 × 10$^4$ | 1.0 × 10$^5$ | 0 |

| Lab# | Sample Identification | | Clostridium difficile ATCC# 9689 cfu/ml | | Fold Growth |
|---|---|---|---|---|---|
| | | | Contact Time 0 Hours | Contact Time 24 Hours | |
| 89639 | Control (Green) | AVG* | 2.7 × 10$^5$ | 2.3 × 10$^6$ | 8.5X |
| QC | In lab untreated fabric | AVG* | 2.6 × 10$^6$ | 4.8 × 10$^7$ | 18X |
| 89641 | B++ Bandage (Thick) | AVG* | 6.5 × 10$^4$ | 1.7 × 10$^5$ | 2.6X |

Figure 6

| Lab# | Sample Identification | | Staphyloccoccus aureus MRSA ATCC# 43300 cfu/ml | | | |
|---|---|---|---|---|---|---|
| | | | Contact Time 0 Hours | Contact Time 6 Hours | Contact Time 18 Hours | Contact Time 24 Hours |
| 89639 | Untreated Control (Green) | AVG* | $1.9 \times 10^6$ | $3.2 \times 10^7$ | $7.5 \times 10^8$ | $2.7 \times 10^9$ |
| | Fold Growth | | NA | 17X | 390X | 1400X |
| 89640 | B++ (White) | AVG* | $1.6 \times 10^6$ | $1.7 \times 10^4$ | $8.5 \times 10^6$ | $4.1 \times 10^6$ |
| | Fold Growth | | NA | -94X | 5X | 2.6X |
| 89641 | B++ Bandage (Thick) | AVG* | $2.1 \times 10^6$ | $6.9 \times 10^5$ | $6.8 \times 10^7$ | $1.2 \times 10^8$ |
| | Fold Growth | | NA | -33X | 32X | 57X |
| QC | In lab untreated fabric | AVG* | $2.0 \times 10^6$ | $6.6 \times 10^6$ | $3.5 \times 10^9$ | $3.7 \times 10^9$ |
| | Fold Growth | | NA | 3.3X | 1750X | 1850X |

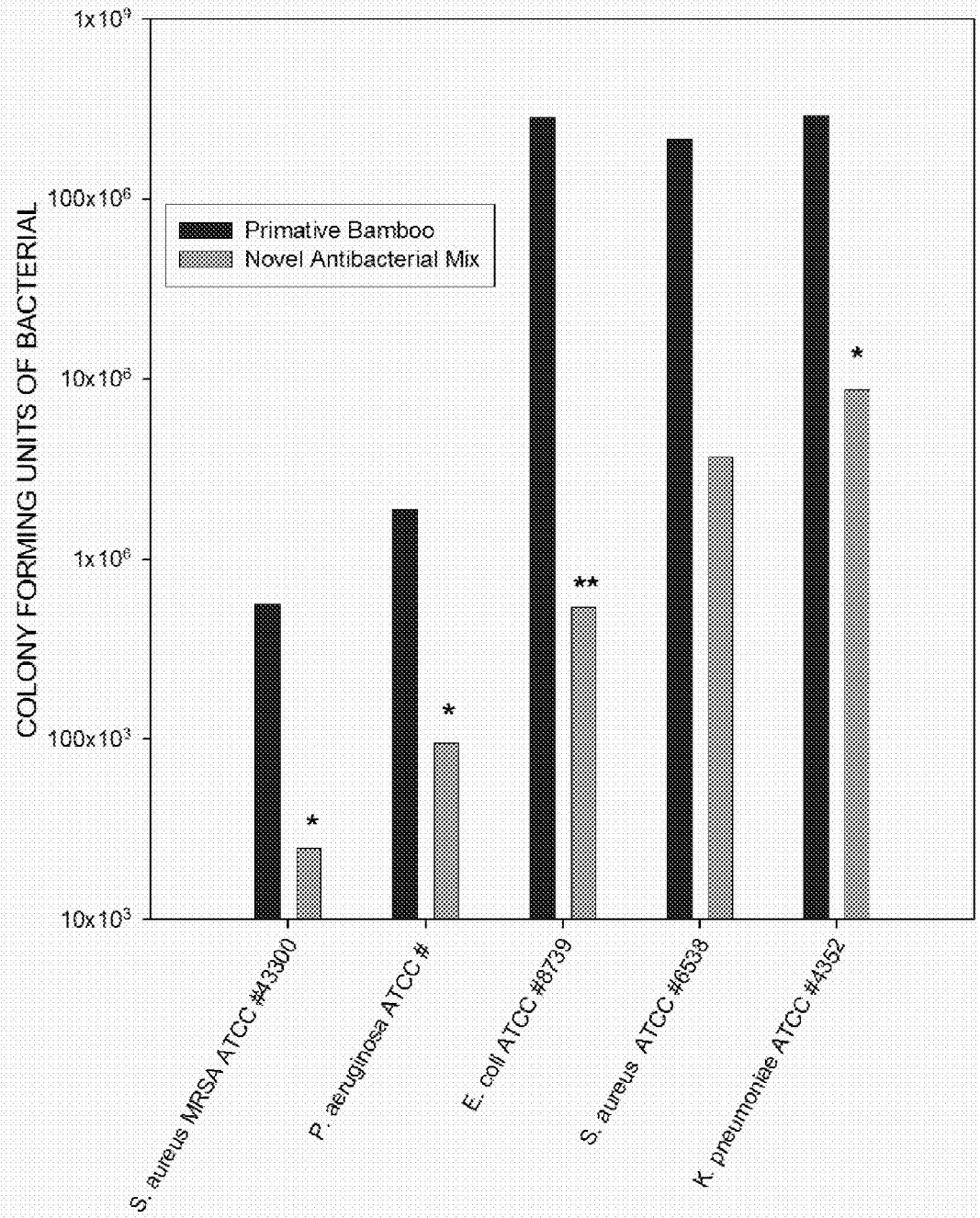

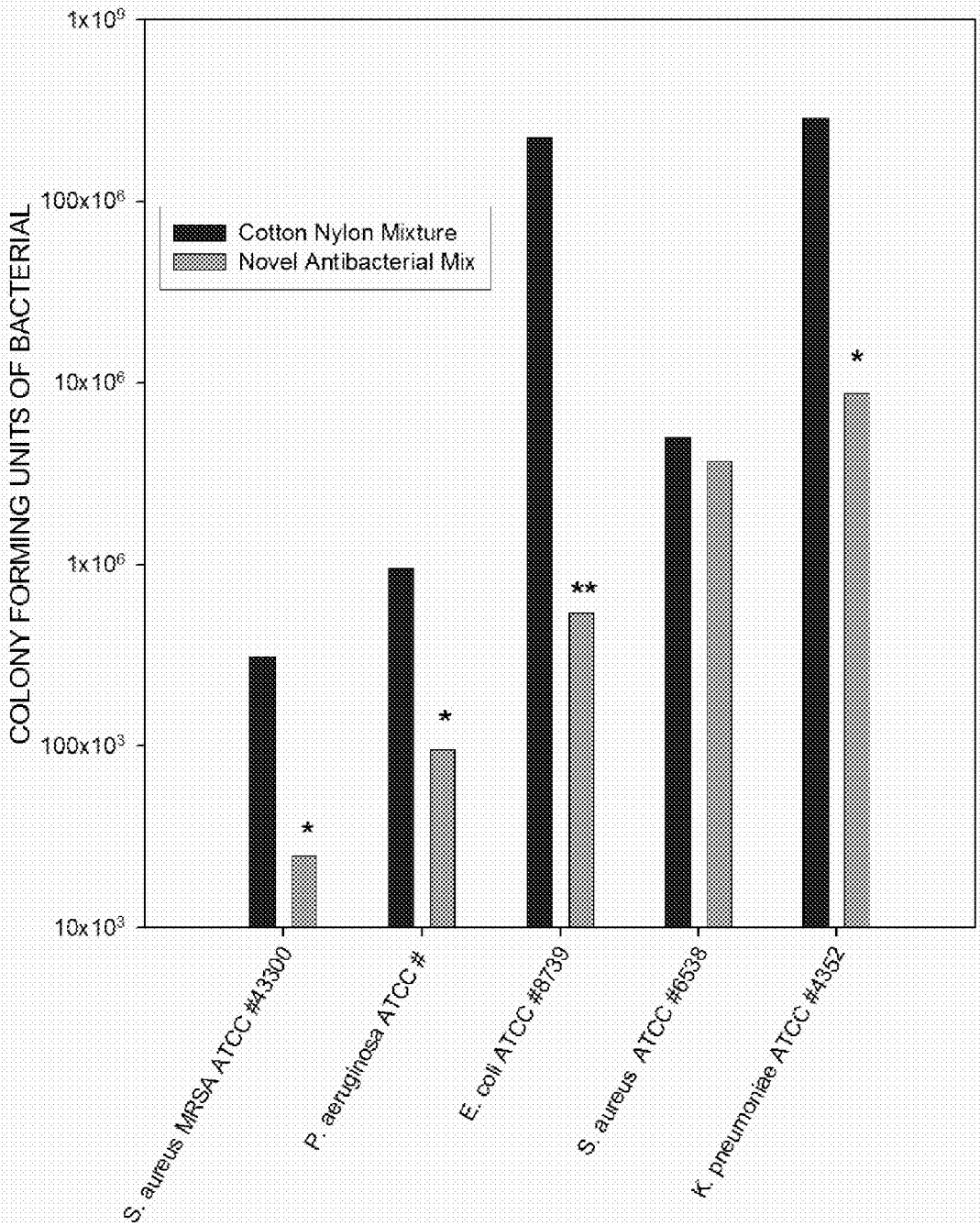

FABRIC WITH ANTIMICROBIAL PROPERTIES

CROSS-REFERENCE TO RELATED APPLICATIONS

This utility patent application claims priority to U.S. provisional patent application Ser. No. 61,372,168 filed on Aug. 10, 2011, which is incorporated by reference herein.

TECHNICAL FIELD

The technology relates to fabrics with antimicrobial properties, in particular, fabrics used as wound dressings or in other situations to reduce chances of infection.

BACKGROUND

The spread of infectious disease through direct skin contact and open wounds is a well-known problem. In addition, the spread of "superbugs" such as methicillin-resistant *Staphylococcus aureus* (MRSA) has become a major problem in U.S.

MRSA can spread in hospitals and other health care facilities, and it can also be picked up in fitness centers, schools, and other public places. MRSA bacteria are resistant to most common antibiotics.

Hospitals typically take precautions to stop the spread of MRSA by stepping up infection control procedures. For example, hospitals implement various infection control procedures that include hand washing, skin disinfectants, sterilization, barrier protection, protective clothing and garments, sterile wound dressings and linen laundering procedures.

Despite these efforts at infection control, certain microbes and bacteria persist and continue to cause infection at an alarming rate. Thus, improvements in products and procedures to further inhibit the spread of infections are desired.

SUMMARY

Antimicrobial and antibacterial textiles can play a part in a strategic plan to reduce healthcare associated infections. The present invention relates to the developments of fabrics, wraps and dressings that have improved antimicrobial/antimicrobial properties by combinations of bamboo, heavy metal and other fibers in the textile product.

The natural antibacterial/antimicrobial properties of bamboo fabric come from inherent qualities of bamboo. One of the compounds found in bamboo is coconut oil, which may contribute to the antimicrobial properties. Bamboo does not require the use of pesticides due to this natural antifungal antibacterial agent. It is rarely attacked by pests or infected by pathogens. The same natural substance that protects bamboo growing in the field, functions in the spun bamboo fibers.

In addition, the anti-infective activity of some heavy metals is well known. For example, heavy metals such as silver have been used as a topical therapy for burn wounds as an antiseptics or disinfectant. Inactivation of bacteria on surfaces containing silver and zinc ions has also been demonstrated.

In one general aspect, a method of producing a fabric with antimicrobial properties includes liquefying bamboo to produce a slurry, adding an antimicrobial element to the slurry, adding a non-bamboo fiber to the slurry to create a mixture and extruding the mixture to produce a fiber.

Embodiments may include one or more of the following features. For example, the method may include crushing the bamboo into fibers or small pieces. Liquefying the bamboo may include adding water and/or a solvent mixture.

The slurry may also be pressurized and/or heated to a high temperature. Impurities can also be removed from the slurry.

The antimicrobial element may be a heavy metal, such as, for example, silver. The silver may be silver ions or silver nanoparticles.

Extruding the mixture may be performed by passing the mixture through spinnerets to create the fiber. The fiber can also be spun to produce a thread and the thread weaved produce the antimicrobial fabric.

In another general aspect, an antimicrobial fabric includes bamboo fiber, a non-bamboo fiber and an antimicrobial element. The antimicrobial element may be a heavy metal such as silver and the non-bamboo fiber may cotton. The antimicrobial fabric may be composed of 69% bamboo, 30% cotton and 1% silver.

DESCRIPTION OF THE DRAWINGS

FIGS. 2-6 are tables that provide test results for the antimicrobial fabric; and FIGS. 7 and 8 are graphs that illustrate test results for the antimicrobial fabric.

DETAILED DESCRIPTION

Figure 1:
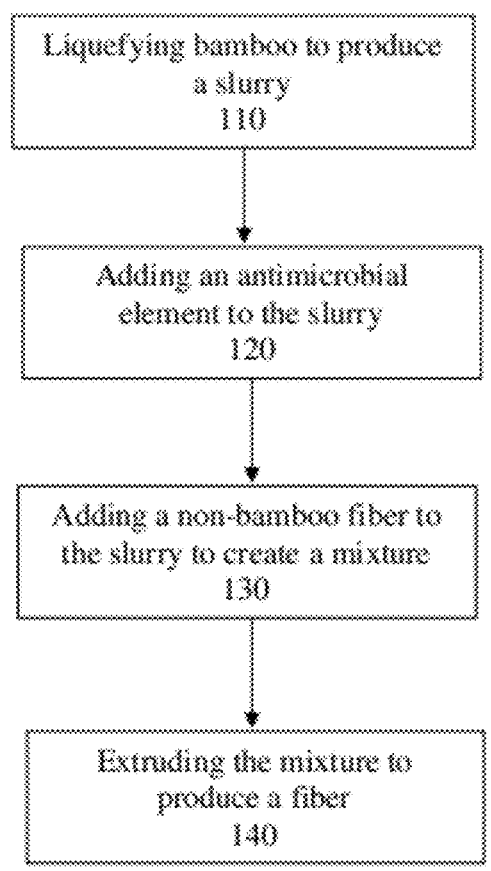
FIG. 1 illustrates a method of producing an antimicrobial fabric.

In one embodiment, a textile with antimicrobial properties is produced by a process described with respect to FIG. 1. First, the bamboo is liquefied into a slurry (operation 110). Typically, the bamboo is crushed into fibers or small pieces. The slurry may be produced by, for example, using water and a solvent mixture. The water and solvents may be added in a vat that is pressurized and heated until the bamboo fibers dissolve.

Impurities are then removed from the slurry. Silver is added to the liquefied bamboo (operation 120). The may be particles or silver nanoparticles are added to the slurry. Silver oxide or silver ions may also be used.

Then, cotton is added to the mixture (operation 130). Other fibers may be added to increase the absorption of silver particles into the fibers.

The composite is then woven into fabric (operation 140). For example, it may be extruded through spinnerets to create a thin and strong fiber. The fibers are then spun into a thread and weaved into the fabric.

The fabric may be further processed such as, for example, dyed to a desired color or cut to size for use in sheets or bandages.

In one of the embodiments of the novel material, the fabric is approximately 69% bamboo, 30% cotton and 1% silver. Other combinations of bamboo, cotton and an antimicrobial element such as a heavy metal may be used. For example, the composition may be 49% bamboo, 50% cotton and 1% silver. In other embodiments, synthetic fibers, such as spandex, may be added to the fabric.

Test reports have demonstrated that the fabric made of bamboo, cotton and silver has improved antimicrobial properties.

FIGS. 2-6 are tables that illustrate test results showing the antibacterial properties of the novel material as compared to other fabrics. Swatches of treated and untreated fabric were cut into 4.8 cm diameter discs which were inoculated with 1 ml of a test organism in a concentration of 1-2×105. Each stack was aseptically transferred to sterile screw cap jars and incubated at 35° C. Treated and untreated samples with no inoculums were also set up as control. After specified time period the set of treated and untreated swatches were removed from the incubator and were neutralized with 100 ml of a neutralizer. Plate counts were performed and incubation was carried out according to requirements for each organism.

Percent reduction of bacteria was calculated by the following formulas:

$$\% R = 100 (B-A)/B$$

where: R: % reduction
- A: the number of bacteria recovered from the inoculated treated test specimen swatches in the jar incubated over the desired contact period
- B: the number of bacteria recovered from the inoculated treated test specimen swatches in the jar immediately after inoculation (at "0" contact time).

The data is presented in Colony Forming Units (CFU)/ml after control and test samples were exposed to organisms. In all cases, the novel material (B++) showed significant inhibition of the four bacterial species tested at 24 hours after inoculation. Additionally, the novel materials showed significant antimicrobial activity at 6 hours after inoculation and two orders of magnitude inhibition at 18 and 24 hours against *Staphylococcus Aureus* MRSA. These results stongly suggest that both the B++ and the treated B++ Bandage could play a significant role in reducing the rate of nosocomial infections.

Another test result is shown graphically in FIGS. 7 and 8. The results shown in FIG. 7 are a comparison of the novel material to bamboo material and cotton-nylon mixtures respectively.

Since certain changes may be made in the above process without departing from the scope of the invention herein involved, it is intended that all matter contained in the above description or shown in the accompanying drawing shall be interpreted in an illustrative and not in a limiting sense. Accordingly, other implementations are within the scope of the following claims.

The invention claimed is:

1. A method of producing a fabric with antimicrobial properties, the method comprising:
   liquefying bamboo to produce a slurry;
   adding silver to the slurry;
   adding a non-bamboo fiber to the slurry to create a mixture; and
   extruding the mixture to produce a fiber;
   wherein the fabric comprises approximately 69% bamboo, 30% cotton and 1% silver.

2. The method of claim 1, further comprising: crushing the bamboo into fibers.

3. The method of claim 1, further comprising: crushing the bamboo into small pieces.

4. The method of claim 1, wherein liquefying bamboo to produce the slurry includes adding water.

5. The method of claim 1, wherein liquefying bamboo to produce the slurry includes adding a solvent mixture.

6. The method of claim 1, wherein liquefying the bamboo further comprises pressurizing the slurry.

7. The method of claim 1, wherein liquefying the bamboo further comprises heating the slurry.

8. The method of claim 1, further comprising: removing impurities from the slurry.

9. The method of claim 1, wherein adding silver comprises adding silver ions to the slurry.

10. The method of claim 1, wherein extruding the mixture comprises extruding the mixture through spinnerets to create the fiber.

11. The method of claim 1, further comprising:
    spinning the fiber to produce a thread; and
    weaving the thread to produce a fabric.

* * * * *